US00PP23598P2

(12) United States Plant Patent
Velderman

(10) Patent No.: US PP23,598 P2
(45) Date of Patent: May 14, 2013

(54) ***HOSTA* PLANT NAMED 'HUDSON BAY'**

(50) Latin Name: ***Hosta sieboldiana* (Tratt.)**
Varietal Denomination: Hudson Bay

(75) Inventor: Linda C. Velderman, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 94 days.

(21) Appl. No.: 13/200,450

(22) Filed: Sep. 23, 2011

(51) Int. Cl.
*A01H 5/00* (2006.01)

(52) U.S. Cl.
USPC ..... Plt./353

(58) Field of Classification Search ..... Plt./353
See application file for complete search history.

*Primary Examiner* — June Hwu

(57) ABSTRACT

A new and distinct *Hosta* plant named 'Hudson Bay', characterized by medium plant size with good growth rate, rounded leaves having very wide blue-green margins, and leaf center that develops to near white center later in season, The near white flowers are held just above the foliage on thick light green-colored scapes in early summer.

1 Drawing Sheet

Botanical classification: *Hosta sieboldiana* (Tratt.).
Variety denomination: 'Hudson Bay'.

BACKGROUND OF THE INVENTION

The present invention relates to the new and distinct *Hosta* plant, *Hosta* 'Hudson Bay' discovered by Linda C. Velderman at a nursery in Zeeland, Mich., USA in the summer of 2007 as an uninduced whole plant mutation in a tissue cultured crop of Hosta 'Eskimo Pie' U.S. Plant Pat. No. 16,290. The new plant has been successfully asexually propagated both by division and by tissue culture at a nursery in Zeeland, Mich. and in both asexual propagation methods found to be stable and produce identical plants that maintain the unique characteristics of the original plant.

BRIEF SUMMARY OF THE INVENTION

*Hosta* 'Hudson Bay' differs from its parent, 'Eskimo Pie', as well as all other *Hostas* known to the applicant. The most similar known *Hosta* cultivars are: 'Dream Weaver' (not patented), 'Eskimo Pie' U.S. Plant Pat. No. 16,290, 'Great American Expectations' (not patented), 'Great Expectations' (not patented), 'Mutley's Rest' (not patented) and 'Thunderbolt' U.S. Plant Pat. No. 14,232. All of the above are from *Hosta sieboldiana* background with creamy-yellow leaf centers and blue-green margins. 'Eskimo Pie', 'Great American Expectations', 'Great Expectations' and 'Mutley's Rest' are all narrower margined forms. 'Mutley's Rest' has a yellow-green center and 'Great Expectations' has a creamy-yellow center which may develop later in the season and with sufficient sunlight to a yellow and cream, respectively. 'Great American Expectations' is supposed to be a faster growing selection from 'Great Expectations' but otherwise identical variegation and leaf color. *Hosta* 'Dream Weaver', 'Dream Queen' and 'Thunderbolt' all have wider blue-green leaf margins than the other comparison plants but the leaf center color is a creamy-yellow developing to a cream. *Hosta* 'Hudson Bay' has similar wider blue-green leaf margins, but it begins the season with leaf centers of creamy white that develop to a near white center.

*Hosta* 'Hudson Bay' compares to *Hosta* 'Dancing Stars' (U.S. Plant Pat. No. 22,611) in having a margin with more blue and near white flowers on scapes that are just above the foliage of the new plant compared to the more green leaf margins and much taller flower scapes of light lavender flowers.

There are over 4,500 cultivars registered with The American *Hosta* Society, which is the International Cultivar Registration Authority for the genus *Hosta*. *Hosta* 'Hudson Bay' differs from these and all unregistered cultivars known to the inventor in the following combined traits:

1. Plant size of medium habit with good growth rate.
2. Foliage with very wide blue-green leaf margins and centers developing from creamy to near white later in the season.
3. Leaf blades developing rugose texture with age.
4. Near white flowers upright scapes just above foliage in early summer.
5. Highly resistant to melting out of the lighter leaf tissue.

BRIEF DESCRIPTION OF THE DRAWINGS

The photographs of the three-year old plant in a garden in Woodbury, Conn. demonstrate the overall appearance of the near-mature plant, including the unique traits, grown in a partially shaded garden in Woodbury, Conn. The colors are as accurate as reasonably possible with color reproductions. Ambient light spectrum, source, direction and temperature may cause the appearance of minor variation in color.

FIG. 1 shows the new plant in a landscape setting early in the growing season, prior to flowering.

DETAILED BOTANICAL DESCRIPTION

The following descriptions and color references are based on The Royal Horticultural Society Colour Chart (2001 edition) except where common dictionary terms are used. The new plant, *Hosta* 'Hudson Bay', has not been observed under all possible environments. The phenotype may vary slightly with different environmental conditions, such as temperature, light, fertility and moisture, but without any change in the genotype. The following observations and size descriptions are of a three-year old plant in a partially shaded landscape as well as two-gallon container greenhouse-grown plants in Zeeland, Mich., USA under 50% shade on cloudless days, with summer day temperatures of 18 to 28 degrees C., and night temperatures of 15 to 20 degrees C.

Botanical classification: *Hosta sieboldiana* (Tratt.).

Cultivar denomination: 'Hudson Bay'.

Parentage: Naturally-occurring whole plant mutation of *Hosta* 'Eskimo Pie' U.S. Plant Pat. No. 16,290.

Propagation: Method by tissue culture and division; time to initiate roots from tissue culture about 20 days from cutting.

Rooting habit: Normal, fleshy, to 3.0 mm thick, lightly branching.

Plant habit: Herbaceous, densely rhizomatous perennial, symmetrical with radical spreading leaves in an arching mound.

Crop time: Under normal summer greenhouse growing conditions about 18 weeks to finish in a one-liter container; plant vigor good.

Plant size: Foliage at flowering is 30.0 to 38.0 cm tall and 60.0 to 65.0 cm wide as a three-year old landscape plant and 25.0 to 30.0 cm tall and 60.0 cm wide for two-year old greenhouse grown plant.

Foliage description:

*Leaf blade*.—Glaucous both upper and lower surfaces; entire; developing rugose with age; broadly ovate to rounded, acute apex and cordate base; Size: 20.0 to 25.0 cm long and 18.0 to 22.0 cm wide for greenhouse grown two-year old plant and 24.0 to 28.0 cm long and 20.0 to 26.0 cm wide for landscape grown three-year old plant; Variegation: variable in width from 3.5 cm to 6.0 cm wide on a greenhouse grown two-year old plant and 4.5 to 7.0 cm wide for landscape grown three-year old plant.

*Leaf color*.—Early spring adaxial margin between RHS 137 B and RHS 137A, early spring adaxial center between RHS 150D and RHS 145D; early spring abaxial margin nearest RHS 138A and early spring abaxial center nearest RHS 145C; mid-season and later adaxial margin nearest RHS 122A with glaucous bloom and RHS 139A once bloom is diminished, mid-season and later adaxial center lighter than RHS 155D; mid-season and later abaxial margin nearest RHS 122A and abaxial center lighter than RHS 155D; intermediate color patterns jetting between the center and the margin on adaxial side of between RHS 139D and RHS 138D the most prominent color and other less prominent colors of RHS 144A and nearest RHS 145C; intermediate color patterns on abaxial side of nearest RHS 144A the most prominent with other smaller bands of nearest RHS 138D.

*Veins*.—Parallel, increasing in number with age, about 14 pairs on either side of mid-rib of three-year old plant; deeply furrowed on adaxial surface and ridged on abaxial surface; lighter than RHS 145 D in leaf center of both adaxial and abaxial surfaces; nearest RHS 138 A in leaf margin of both surfaces.

*Petioles*.—Convex, 15 to 20 cm long and about 13.0 mm wide for two-year old greenhouse grown plant and 20 to 28 cm tall for a three-year old landscape grown plant.

*Petiole color*.—Adaxial and abaxial margin near leaf base nearest RHS N138A and lightening to nearest RHS N138C near soil line; center adaxial nearest RHS 145D and abaxial center nearest RHS 138D.

*Flower description*.—26 to 30 per scape, funnelform, about 6.5 cm wide and 8.5 cm long, (distal flowers smaller), persists for up to two days, scapes remain effective from mid June to early July; no significant floral fragrance detected.

*Buds*.—Clavate, one to two days prior to opening buds are about 7.5 cm long and 1.7 cm diameter at widest point, clavate constricting to a claw of about 4.0 mm in diameter at base; lighter than RHS 76D.

*Tepals*.—Six, fused in the basal half to two-thirds, acute apex, approximately 8.5 cm long and 1.3 cm wide, arranged in two layers of three, the inner three with clear 1 to 2 mm margin, Petal color; adaxial center of tepals RHS 76 D and violet stripes RHS 76 C; basal one-third and margins white, lighter than RHS 155D or RHS 76D; abaxial center is pale lavender, lighter than RHS 76D and margins and basal half white, lighter than either RHS 155D or RHS 76D.

*Peduncle*.—Cylindrical, erect, nearly vertical; about 42.0 cm tall and 0.8 cm in diameter at base.

*Peduncle color*.—Between RHS 138 A to RHS 139 A.

*Pedicel*.—Curved, 15 mm long, 3 mm wide, nearest RHS 138 D.

*Gynoecium*.—Style: single, about 7.0 cm long and 1.0 mm in diameter; nearest RHS 155D, curved upward at distal 8.0 mm; Stigma: globose to about 2.0 mm in diameter; white, lighter than RHS 155D; Ovary: superior, oblong, about 6.0 mm long and 3.0 mm diameter; nearest RHS 138C.

*Androecium*.—Filaments — six, white, lighter than RHS 155D, about 6.0 cm long and 1.0 mm in diameter; Anthers: dorsifixed, oblong, about 6.0 mm long and 1.5 mm in diameter; nearest RHS 79 A; Pollen: globose; nearest RHS 17 A.

Fruit and seeds have not yet been observed.

Disease and pest resistance: The plant is more resistant to melting-out than most other light-centered varieties. Disease and pest resistance beyond that of other thick-leafed cultivars has not been noted, but shows little to no feeding from slugs under conditions that thinner-leafed *Hostas* would show feeding. It grows best with plenty of moisture and good drainage but is able to tolerate some drought. Hardiness from at least USDA zone 3 through zone 9.

I claim:

1. A new and distinct cultivar of ornamental *Hosta* plant named 'Hudson Bay' as herein described and illustrated, suitable as a potted plant, for landscaping specimen or in mass, and for fresh-cut flower and foliage arrangements.

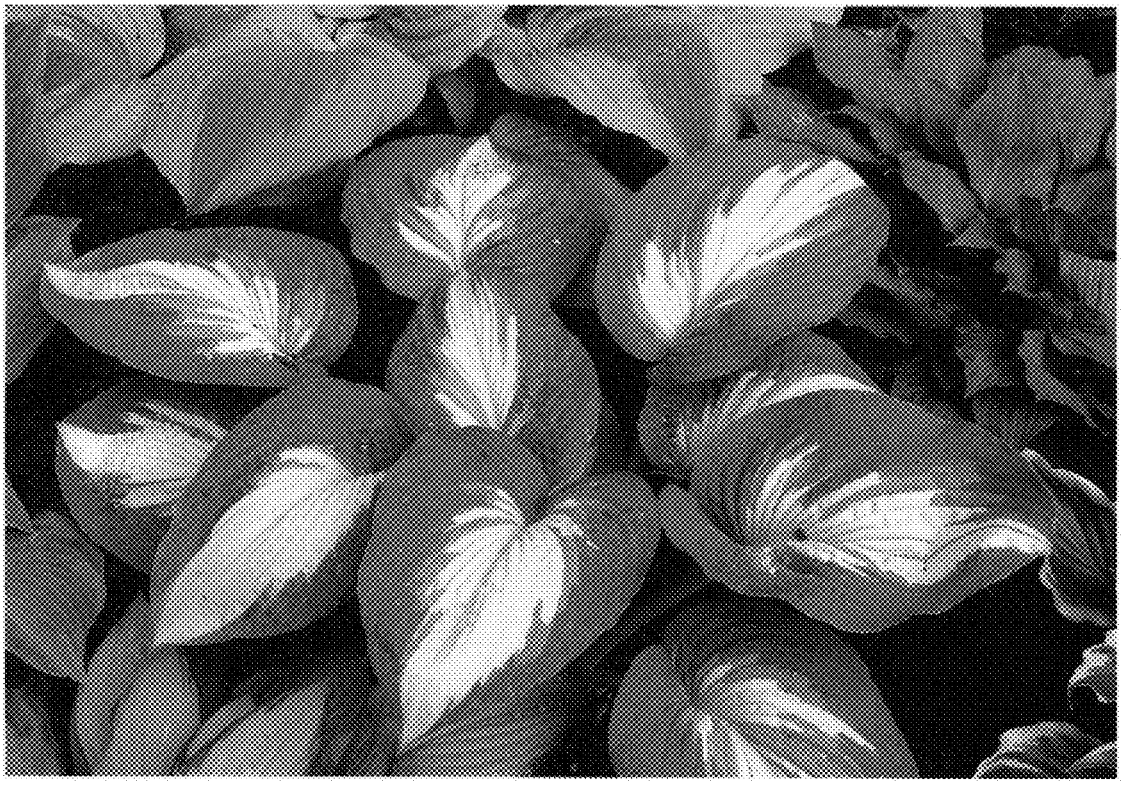

* * * * *